United States Patent
Dai et al.

(10) Patent No.: US 10,800,745 B2
(45) Date of Patent: Oct. 13, 2020

(54) METHODS FOR 1,4-DIAZO N-HETEROCYCLE SYNTHESIS

(71) Applicant: Purdue Research Foundation, West Lafayette, IN (US)

(72) Inventors: Mingji Dai, West Lafayette, IN (US); Zhishi Ye, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/034,412

(22) Filed: Jul. 13, 2018

(65) Prior Publication Data

US 2019/0055205 A1  Feb. 21, 2019

Related U.S. Application Data

(60) Provisional application No. 62/547,127, filed on Aug. 18, 2017.

(51) Int. Cl.
| | |
|---|---|
| *C07D 241/50* | (2006.01) |
| *C07D 241/04* | (2006.01) |
| *C07D 401/06* | (2006.01) |
| *C07D 405/06* | (2006.01) |
| *C07D 403/06* | (2006.01) |
| *C07D 401/12* | (2006.01) |
| *C07D 471/04* | (2006.01) |
| *C07D 407/12* | (2006.01) |
| *C07F 9/6509* | (2006.01) |
| *C07D 487/04* | (2006.01) |
| *C07D 243/08* | (2006.01) |
| *C07D 243/10* | (2006.01) |
| *C07D 245/02* | (2006.01) |
| *C07D 405/12* | (2006.01) |
| *C07F 9/645* | (2006.01) |

(52) U.S. Cl.
CPC ......... *C07D 241/50* (2013.01); *C07D 241/04* (2013.01); *C07D 243/08* (2013.01); *C07D 243/10* (2013.01); *C07D 245/02* (2013.01); *C07D 401/06* (2013.01); *C07D 401/12* (2013.01); *C07D 403/06* (2013.01); *C07D 405/06* (2013.01); *C07D 405/12* (2013.01); *C07D 407/12* (2013.01); *C07D 471/04* (2013.01); *C07D 487/04* (2013.01); *C07F 9/645* (2013.01); *C07F 9/650952* (2013.01)

(58) Field of Classification Search
CPC .......................... C07D 241/02; C07D 295/08
See application file for complete search history.

(56) References Cited

FOREIGN PATENT DOCUMENTS

| JP | 2000007664 | * | 1/2000 | ............ C07B 53/00 |
|---|---|---|---|---|
| WO | WO 2008049919 | * | 5/2008 | |
| WO | WO 2014060770 | * | 4/2014 | |

OTHER PUBLICATIONS

Macleod. Synlett, 2009, 17, 2857-61 (Year: 2009).*
Revesz. TetrahedronL Letters, 2005, 46, 5577-5580 (Year: 2005).*
Jia. Bioorganic and Medicinal Chemistry Letters, 2004, 14, 2073-78 (Year: 2004).*
Lukina. Tetranderon Letters, 2006, 47 , 51-54 (Year: 2006).*
Lukina. Tetrahedron Letters, 2005, 46, 1205-1207 (Year: 2005).*
"phosphono", 1995, accessed Nov. 22, 2019 (Year: 1995).*
March. Advanced Organic Chemistry, 1992, pp. 428-429). (Year: 1992).*
Bera. ACS Combinatorial Sciences, 2012, 14, 1-4 (Year: 2012).*
Ye. Nature Communications, 2018, 9:721, 1-11 (Year: 2018).*
"Periodic table", http://www.chem.qmul.ac.uk/iupac/AtWt/table.html, 2016 (Year: 2016).*

* cited by examiner

*Primary Examiner* — Noble E Jarrell
(74) *Attorney, Agent, or Firm* — Purdue Research Foundation; Zhigang Rao

(57) ABSTRACT

The present disclosure relates to novel synthetic method of making 1, 4-diazo N-heterocycles via intermolecular amphoteric diamination of allenes, and to the compounds made by the novel synthetic method.

3 Claims, No Drawings

METHODS FOR 1,4-DIAZO N-HETEROCYCLE SYNTHESIS

CROSS-REFERENCE TO RELATED APPLICATION

This application claims the benefits of U.S. Provisional Application Ser. No. 62/547,127, filed Aug. 18, 2017. The contents of which are incorporated herein entirely.

GOVERNMENT RIGHTS

This invention was made with government support under Award No. P30CA023168 awarded by the National Institutes of Health (NIH) and under Grant No. CHE 1625543 awarded by the National Science Foundation (NSF). The government has certain rights in the invention.

TECHNICAL FIELD

The present disclosure relates to novel synthetic methods of making 1,4-diazo N-heterocycles via intermolecular amphoteric diamination of allenes, and relates to the compounds made by the novel synthetic method.

BACKGROUND

This section introduces aspects that may help facilitate a better understanding of the disclosure. Accordingly, these statements are to be read in this light and are not to be understood as admissions about what is or is not prior art.

More than half of the FDA-approved small-molecule therapeutics contain at least one N-heterocycles. Among N-heterocycles, the saturated 1,4-diazo heterocycles including piperazine, 1,4-diazepane, and 1,4-diazocane are highly important for the development of new therapeutics. However, there is a significant lack of structural diversity of these 1,4-diazo heterocycles, especially their substation pattern on the carbon atoms, due to the lack of efficient methods or the synthetic limitations of the existing methods to synthesize these N-heterocycles.

Novel synthetic method to prepare novel diazo heterocycles are therefore needed.

SUMMARY

The present disclosure provides novel and convenient amphoteric diamination strategy to synthesize carbon-substituted 1,4-diazo N-heterocycles in a one-pot reaction. This strategy assembles readily available 1,2-, 1,3- or 1,4-diamine derivatives with electron-deficient allenes via a formal [n+2] (n=4, 5, 6) cyclization mode with an appropriate reagents such as N-iodosuccinimide (NIS) or a combination of N-chlorosuccinimide and KI to produce various piperazines, 1,4-diazepanes, and 1,4-diazocanes, respectively. The reaction features mild reaction conditions, high functional group tolerance, and scalability (gram scale). The reagents are cheap and readily available and no precious transition metal catalysts are needed. In addition to a direct one-pot reduction to the corresponding fully saturated N-heterocycles, the present disclosure also demonstrated that the primary vinylogous amide products can be converted to much more sophisticated products by using a trifluoromethyl addition or an intromolecular Mannich reaction.

The present invention provides compounds with novel structures that may possess one or more of the following activities: antibacterial, antifungal, antiviral, anticancer, and antiparasitic activity. The compounds disclosed in the present disclosure may also be used for the compound building block for the development of new therapeutics. Specifically, the compounds of the present invention are represented in Formula I below:

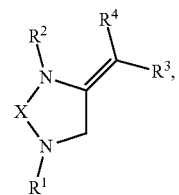

or any derivative or salt thereof, wherein $R^1$ is $R^5$—S(=O)$_2$—, or a nitrogen protecting group selected from the group consisting of acetyl (Ac), trifluoroacetyl (TFA), trichloroacetyl (TCA), tert-butyloxycarbonyl (Boc), carbobenzyloxy (Cbz), vinyloxycarbonyl (Voc), allyloxycarbonyl (Alloc), and 9-fluorenylmethyloxycarbonyl (Fmoc);

$R^2$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, wherein one or more hydrogen is optionally substituted by an optionally substituted aryl, heteroaryl, $C_3$-$C_{10}$ cycloalkyl, $C_3$-$C_{10}$ hetero cycloalkyl, F, Cl, Br, I, hydroxyl, $C_1$-$C_8$ alkoxyl, amino group, or NHBoc, or $R^2$ may form a fused ring with one adjacent carbon atom next to the nitrogen that $R^2$ is attached;

$R^3$ and $R^4$ are each independently H, optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, or an electro withdrawing group (EWG), wherein at least one of $R^3$ and $R^4$ is an electro withdrawing group.

$R^5$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, aryl, heteroaryl; and X is a $C_2$-$C_4$ saturated carbon linker, wherein $C_2$-$C_4$ saturated carbon linker is optionally substituted with 4-8 hydrogen, 4-8 optionally substituted $C_1$-$C_{12}$ straight or branched alkyl, wherein one of the 4-8 optionally substituted $C_1$-$C_{12}$ straight or branched alkyl may form a fused ring with the $C_2$-$C_4$ saturated carbon linker or with $R_1$, or from a spiro ring with the carbon atom on the $C_2$-$C_4$ saturated carbon linker that the straight or branched alkyl is attached.

In one embodiment, the present disclosure provides methods of making N-heterocycles via intermolecular amphoteric diamination of allenes.

In one embodiment, the present disclosure provides methods of using compounds of N-heterocycles made via intermolecular amphoteric diamination of allenes for the development of new therapeutics.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons (C$_6$-C$_{14}$) or from 6 to 10 carbon atoms (C$_6$-C$_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

As used herein, the term "salts" and/or "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

As used herein, the term "nitrogen-protecting group" in the present disclosure may be any functional group that can make the amine nitrogen to be protected as any form of carbamate, benzyl amine, amide, thioamide, sulfonamide, urea, or thiourea. The nitrogen-protecting group may include but is not limited to benzoyl, benzyloxycarbonyl, t-butoxycarbonyl, benzene sulfonyl, toluene sulfonyl, benzyl, benzhydryl, trityl, acetyl, or trifluoroacetyl.

As used herein, the term "electron withdrawing group (EWG)" in the present disclosure may be any functional group that removes electron density from a π system, such as the conjugated carbon-carbon double bond system, making the π system more electrophilic. In the present disclosure, an electron withdrawing group may be but is not limited to aldehyde group, ketone group, carboxylic acid group, acyl group, ester group, amide group, trihalide group, cyano group, sulfonyl group, phosphono group, nitro group, F, or Cl.

As used herein, the term "1,4-diazo N-heterocycles" refers to a compound comprising a nitrogen-containing ring wherein the ring comprises two nitrogen atoms and the two nitrogen atoms are separated by a linker comprising two carbons from at least one side of the nitrogen-containing ring.

The present invention provides compounds with novel structures that may possess one or more of the following activities: antibacterial, antifungal, antiviral, anticancer, and antiparasitic activity. Specifically, the compounds of the present invention are represented in Formula I below:

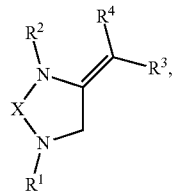

I or any derivate or salt thereof, wherein
$R^1$ is $R^5$—S(=O)$_2$—, or a nitrogen protecting group selected from the group consisting of acetyl (Ac), trifluoroacetyl (TFA), trichloroacetyl (TCA), tert-butyloxycarbonyl (Boc), carbobenzyloxy (Cbz), vinyloxycarbonyl (Voc), allyloxycarbonyl (Alloc), and 9-fluorenylmethyloxycarbonyl (Fmoc);
$R^2$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, wherein one or more hydrogen is optionally substituted by an optionally substituted aryl, heteroaryl, $C_3$-$C_{10}$ cycloalkyl, $C_3$-$C_{10}$ hetero cycloalkyl, F, Cl, Br, I, hydroxyl, $C_1$-$C_8$ alkoxyl, amino group, or NHBoc, or $R^2$ may form a fused ring with one adjacent carbon atom next to the nitrogen that $R^2$ is attached;
$R^3$ and $R^4$ are each independently H, optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, or an electro withdrawing group (EWG), wherein at least one of $R^3$ and $R^4$ is an electro withdrawing group.
$R^5$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, aryl, heteroaryl; and
X is a $C_2$-$C_4$ saturated carbon linker, wherein $C_2$-$C_4$ saturated carbon linker is optionally substituted with 4-8 hydrogen, 4-8 optionally substituted $C_1$-$C_{12}$ straight or branched alkyl, wherein one of the 4-8 optionally substituted $C_1$-$C_{12}$ straight or branched alkyl may form a fused ring with the $C_2$-$C_4$ saturated carbon linker or with $R_1$, or from a spiro ring with the carbon atom on the $C_2$-$C_4$ saturated carbon linker that the straight or branched alkyl is attached.

In one embodiment, the present invention provides a compound of Formula I, wherein $R^1$ is $R^5$—S(=O)$_2$—, and $R^5$ is selected from the group consisting of:

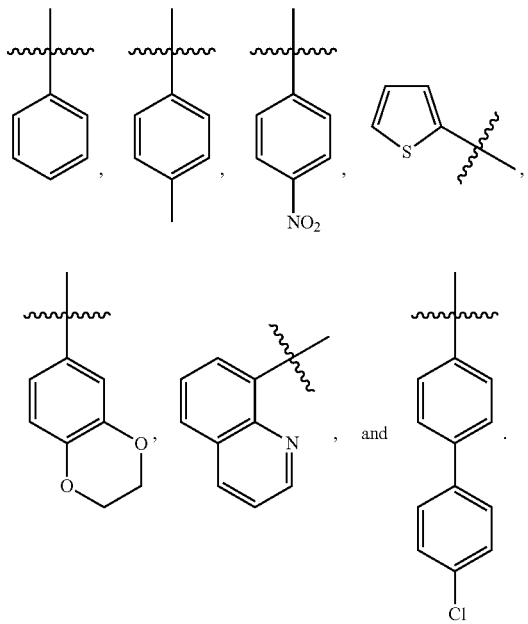

In one embodiment, the present invention provides a compound of Formula I, wherein $R^2$ is optionally substituted $C_1$-$C_{12}$ straight or branched alkyl, $C_1$-$C_{12}$ alkenyl, $C_3$-$C_{10}$ cycloalkyl, wherein one or more hydrogen of the $C_1$-$C_{12}$ straight or branched alkyl, $C_1$-$C_{12}$ alkenyl, or $C_3$-$C_{10}$ cycloalkyl is optionally substituted with a benzene ring, quinolin ring, pyrrol ring, furan ring, or indole ring, wherein the benzene ring, quinolin ring, pyrrol ring, furan ring, or indole ring is further optionally substituted with 1-3 $C_1$-$C_6$ alkyl, halide, $C_1$-$C_4$ alkoxyl, trihalide methyl, or nitro group.

In one embodiment, the present invention provides a compound of Formula I, wherein electro withdrawing group (EWG) is selected from the group consisting of aldehyde group, ketone group, carboxylic acid group, acyl group, ester group, amide group, trihalide group, cyano group, sulfonyl group, phosphono group, nitro group, F, and $C_1$.

In one embodiment, the present invention provides a compound of Formula I, wherein electro withdrawing group (EWG) is may be but is not limited to methoxycarbonyl, ethoxycarbonyl, butoxycarbonyl, t-butoxycarbonyl, phenoxycarbonyl, (3-methoxyphenoxy)carbonyl, ((3-methoxybenzyl)oxy)carbonyl, furan-2-carbonyl, benzoyl, fluorobenzoyl, chlorobenzoylmethoxybenzoyl, trifluoromethylbenzoyl, diethoxyphosphoryl, diphenylphosphoryl, phenylsulfonyl, cyano, or 2-oxy-4-phenylbutyl.

In one embodiment, the present invention provides a compound of Formula II:

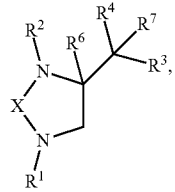

or any derivative or salt thereof, wherein $R^1$ is $R^5$—S(=O)$_2$—, or a nitrogen protecting group selected from the group consisting of acetyl (Ac), trifluoroacetyl (TFA), trichloroacetyl (TCA), tert-butyloxycarbonyl (Boc), carbobenzyloxy (Cbz), vinyloxycarbonyl (Voc), allyloxycarbonyl (Alloc), and 9-fluorenylmethyloxycarbonyl (Fmoc);

$R^2$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, wherein one or more hydrogen is optionally substituted by an optionally substituted aryl, heteroaryl, $C_3$-$C_{10}$ cycloalkyl, $C_3$-$C_{10}$ hetero cycloalkyl, F, Cl, Br, I, hydroxyl, $C_1$-$C_8$ alkoxyl, amino group, or NHBoc, or $R^2$ may form a fused ring with one adjacent carbon atom next to the nitrogen that $R^2$ is attached;

$R^3$ and $R^4$ are each independently H, optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, or an electro withdrawing group (EWG), wherein at least one of $R^3$ and $R^4$ is an electro withdrawing group.

$R^5$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, aryl, heteroaryl;

$R^6$ is H, nitro, F, Cl, Br, I, amino, cyano, $C_1$-$C_4$ straight, branched, or cycloalkyl, $C_1$-$C_4$ trifluoroalkyl, hydroxyl, $C_1$-$C_4$ alkoxyl, or —SH;

$R^7$ is H, $C_1$-$C_4$ straight, branched, or cycloalkyl; and

X is a $C_2$-$C_4$ saturated carbon linker, wherein $C_2$-$C_4$ saturated carbon linker is optionally substituted with 4-8 hydrogen, 4-8 optionally substituted $C_1$-$C_{12}$ straight or branched alkyl, wherein one of the 4-8 optionally substituted $C_1$-$C_{12}$ straight or branched alkyl may form a fused ring with the $C_2$-$C_4$ saturated carbon linker or with $R_1$, or from a spiro ring with the carbon atom on the $C_2$-$C_4$ saturated carbon linker that the straight or branched alkyl is attached In one embodiment, the present invention provides a compound of Formula II:

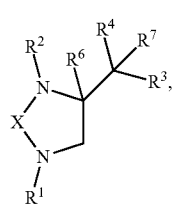

wherein the compound is selected from the group consisting of:

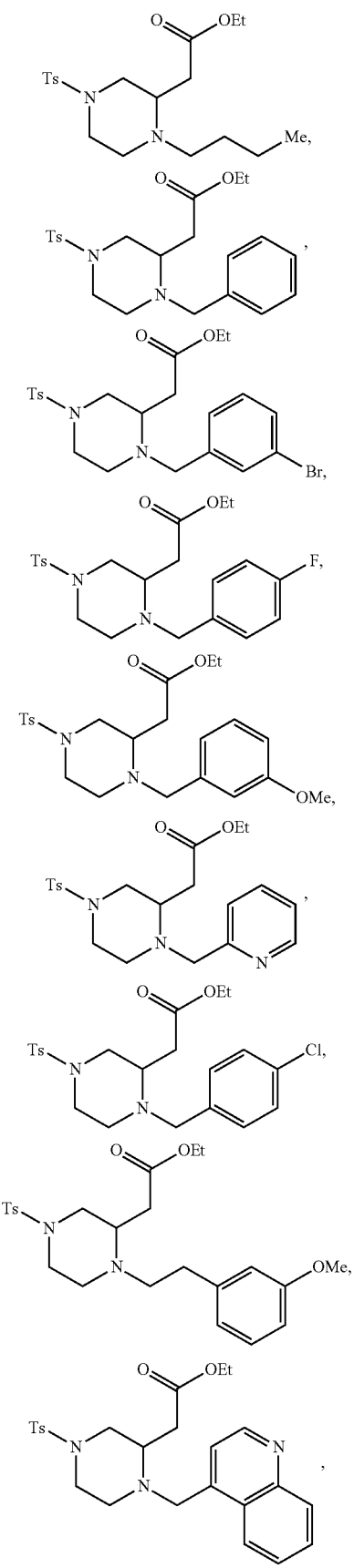

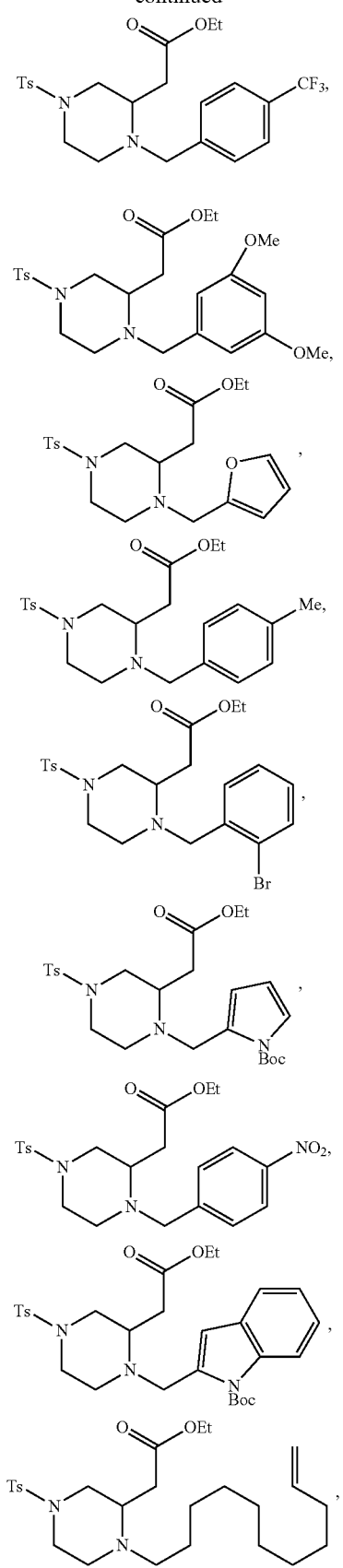
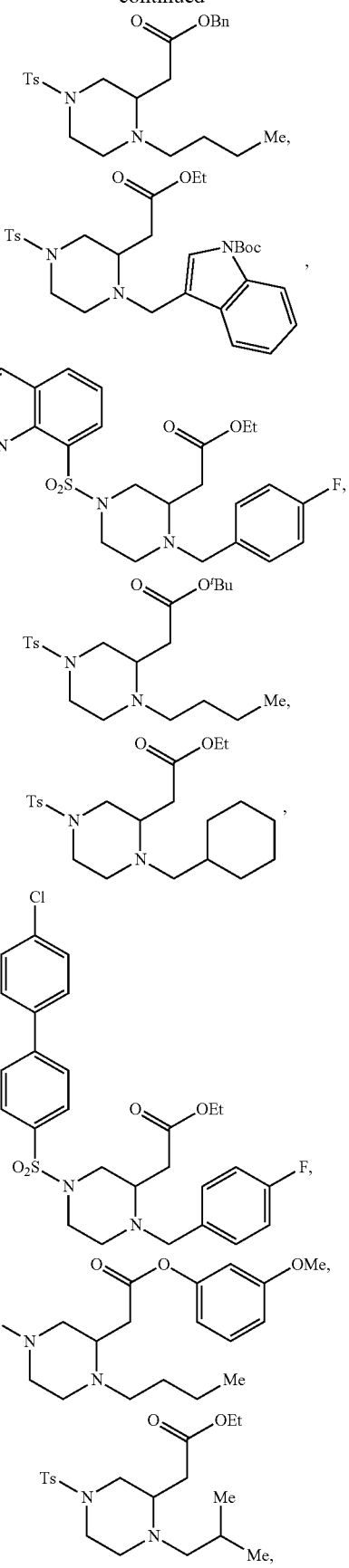

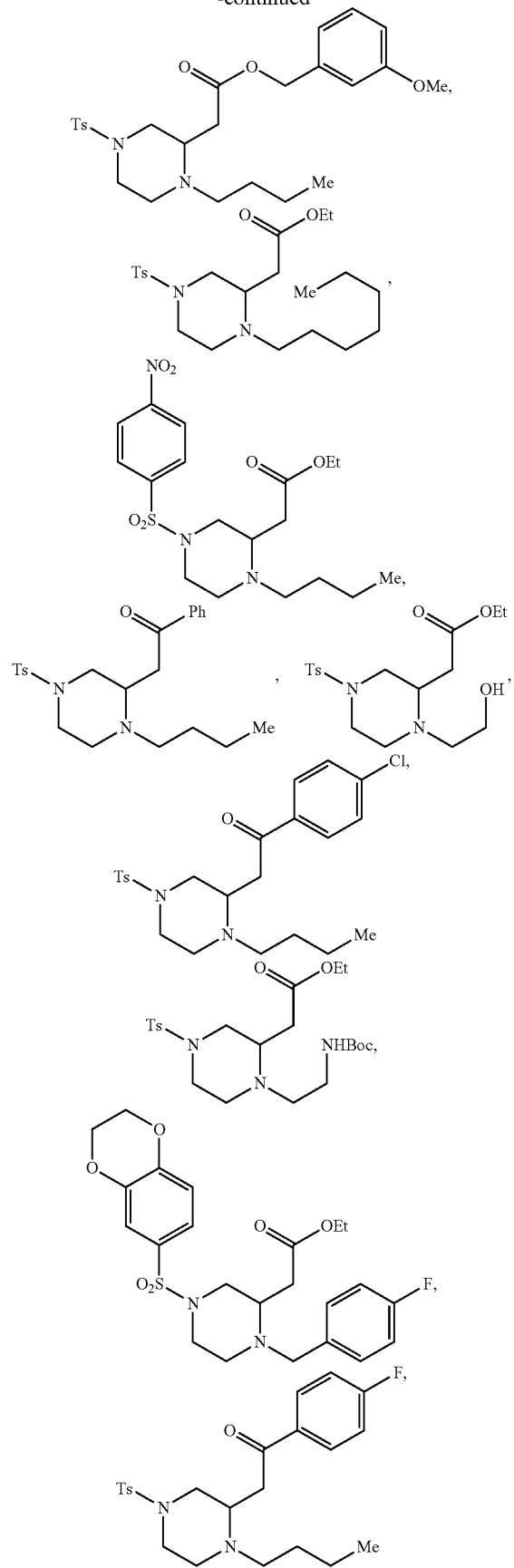
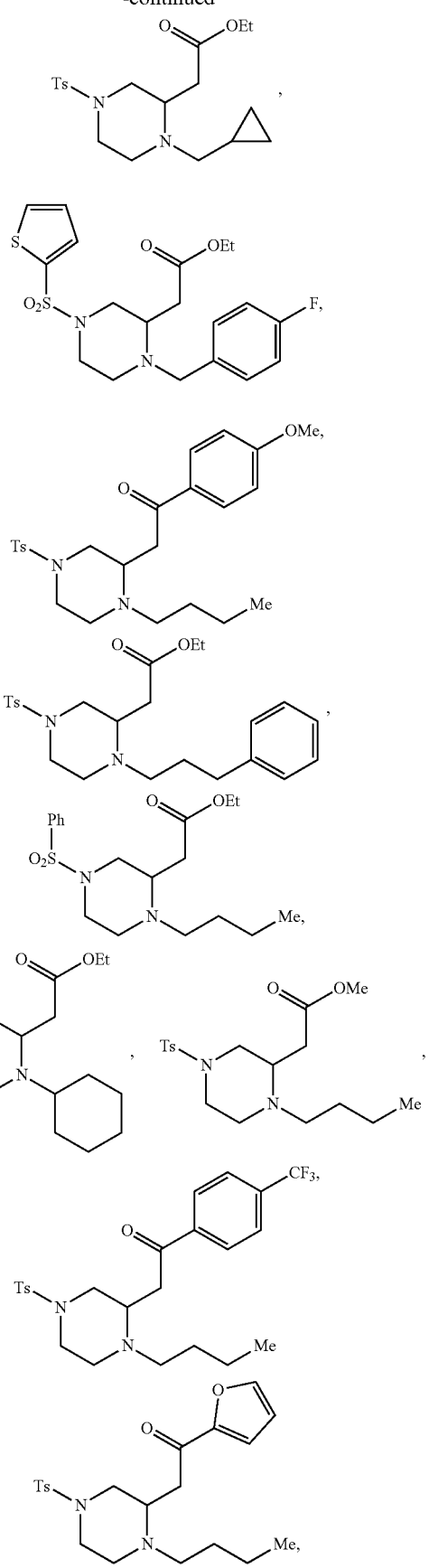

-continued
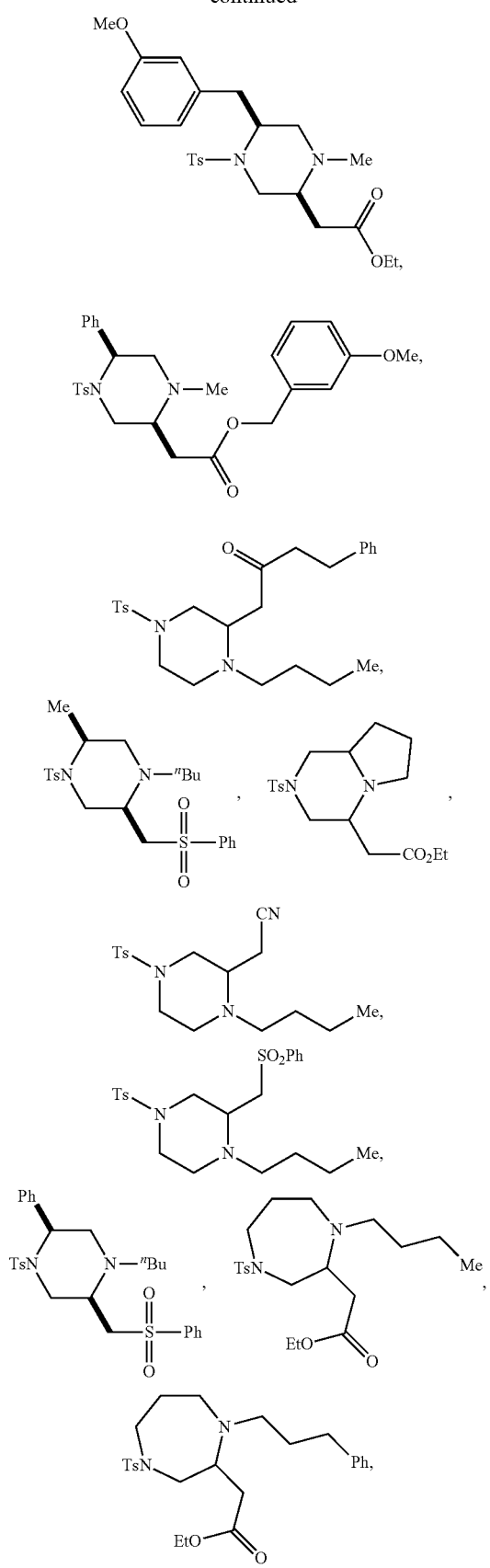
-continued
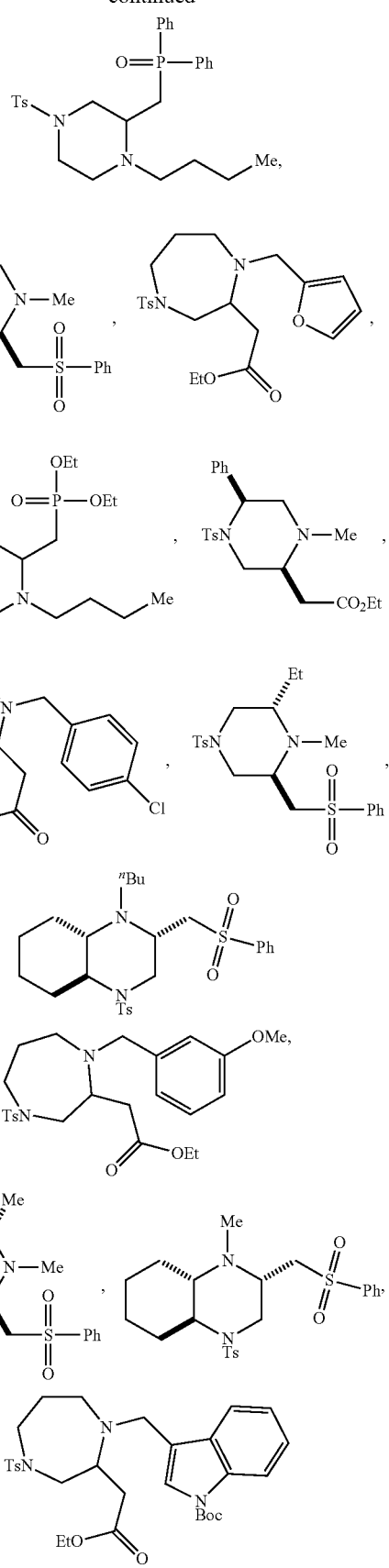

-continued
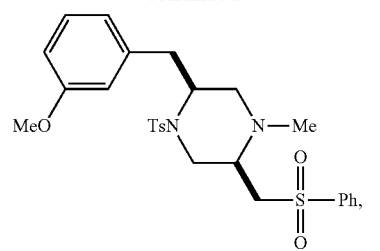
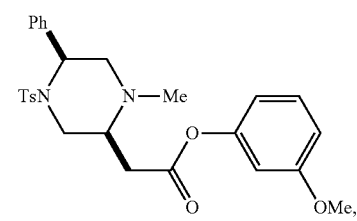
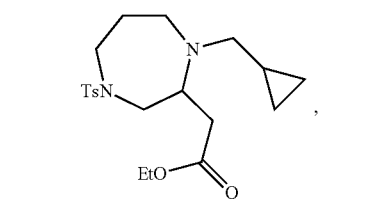
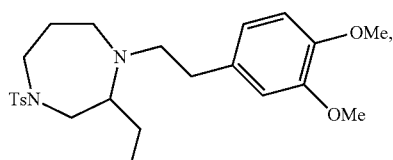
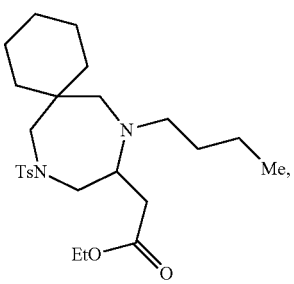
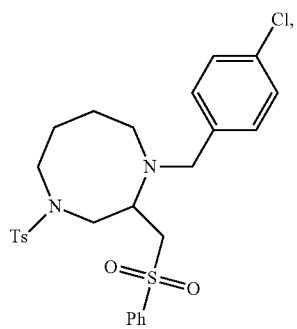
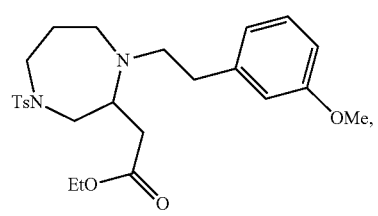
-continued
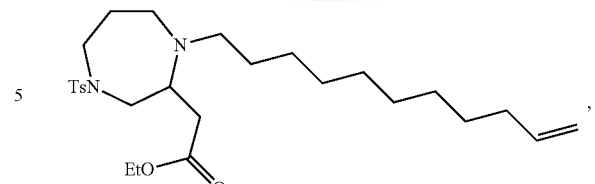
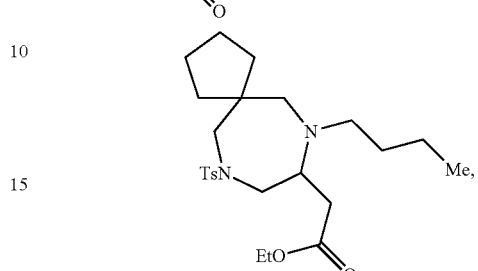
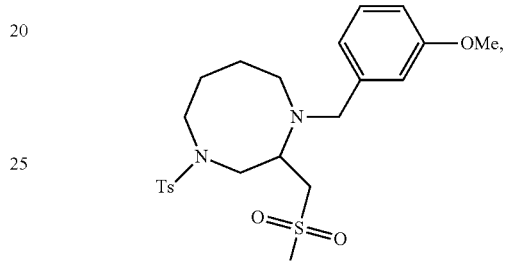
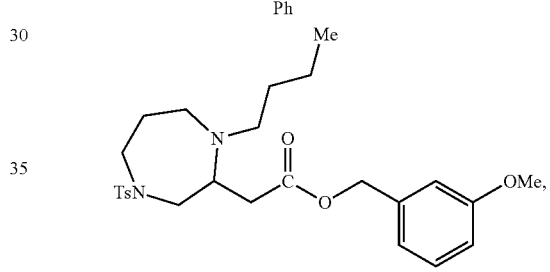
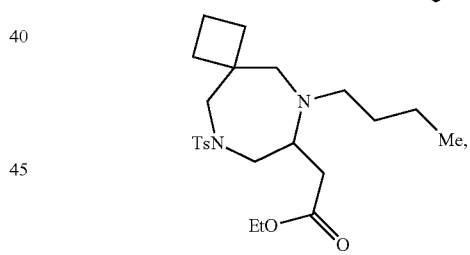
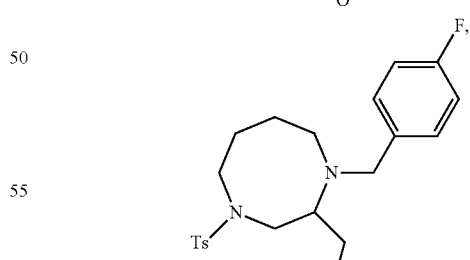
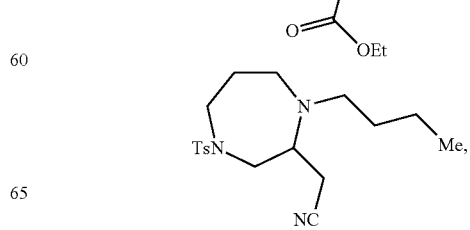

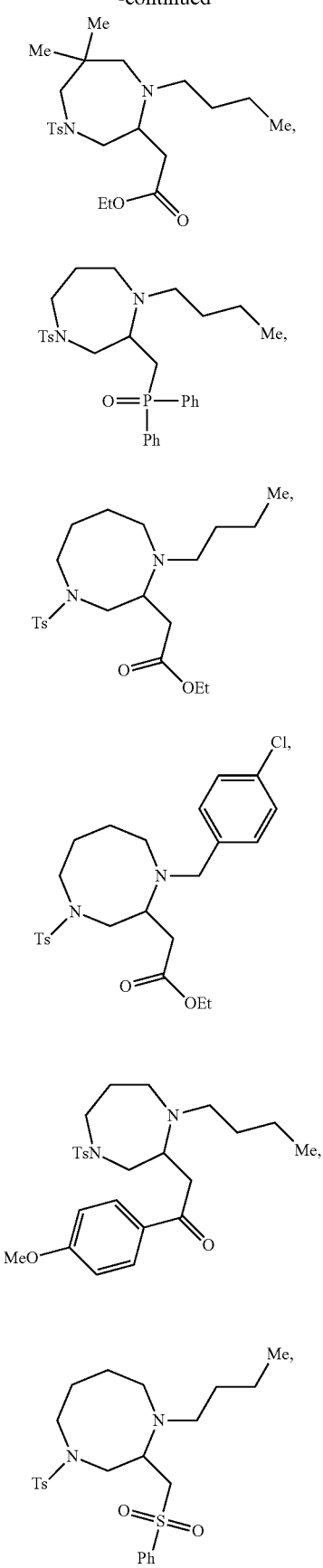
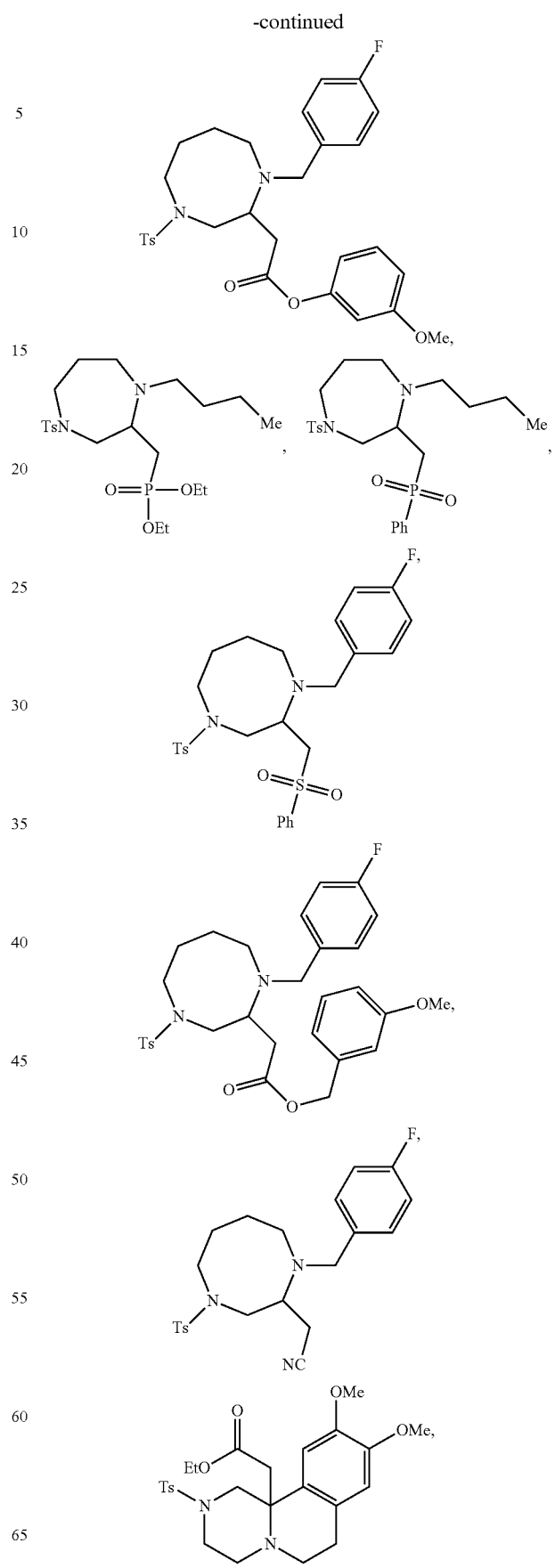

-continued

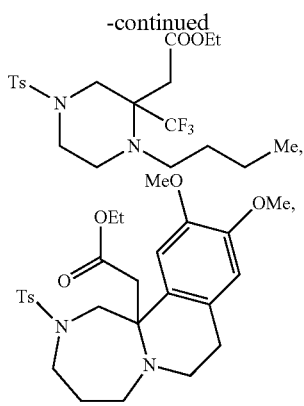

any derivative or salt thereof.

In one embodiment, the present invention provides a method of preparing a compound of Formula I comprising reacting a compound of $R^1NHXNYR^2$ with a compound of $CH_2=C=CR^3R^4$:

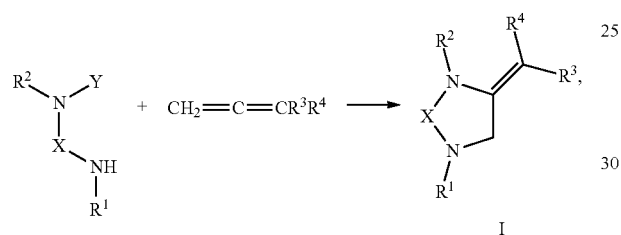

or any derivative or salt thereof, wherein

R$^1$ is $R^5$—S(=O)$_2$—, or a nitrogen protecting group selected from the group consisting of acetyl (Ac), trifluoroacetyl (TFA), trichloroacetyl (TCA), tert-butyloxycarbonyl (Boc), carbobenzyloxy (Cbz), vinyloxycarbonyl (Voc), allyloxycarbonyl (Alloc), and 9-fluorenylmethyloxycarbonyl (Fmoc);

R$^2$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, wherein one or more hydrogen is optionally substituted by an optionally substituted aryl, heteroaryl, $C_3$-$C_{10}$ cycloalkyl, $C_3$-$C_{10}$ hetero cycloalkyl, F, Cl, Br, I, hydroxyl, $C_1$-$C_8$ alkoxyl, amino group, or NHBoc, or R$^2$ may form a fused ring with one adjacent carbon atom next to the nitrogen that R$^2$ is attached;

R$^3$ and R$^4$ are each independently H, optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, or an electro withdrawing group (EWG), wherein at least one of R$^3$ and R$^4$ is an electro withdrawing group;

R$^5$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, aryl, heteroaryl;

X is a $C_2$-$C_4$ saturated carbon linker, wherein $C_2$-$C_4$ saturated carbon linker is optionally substituted with 4-8 hydrogen, 4-8 optionally substituted $C_1$-$C_{12}$ straight or branched alkyl, wherein one of the 4-8 optionally substituted $C_1$-$C_{12}$ straight or branched alkyl may form a fused ring with the $C_2$-$C_4$ saturated carbon linker or with R$_1$, or from a spiro ring with the carbon atom on the $C_2$-$C_4$ saturated carbon linker that the straight or branched alkyl is attached; and Y is H, Cl, Br, or I.

In one embodiment, the present invention provides a method of preparing a compound of Formula I comprising reacting a compound of $R^1NHXNYR^2$ with a compound of $CH_2=C=CR^3R^4$, wherein the substitution groups are defined as in the previous paragraphs, wherein the reaction condition comprising the use of an appropriate base and an appropriate halide ion. In one aspect, the halide ion is iodide ion (I$^-$). In one aspect, an appropriate base may be but is not limited to $Cs_2CO_3$.

In one embodiment, the present invention provides a method of preparing a compound of Formula II from a compound of Formula I:

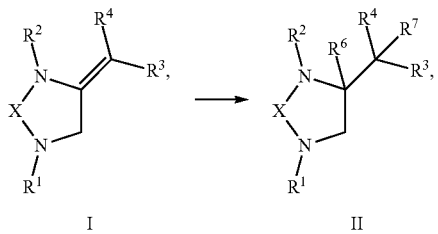

or any derivative or salt thereof, wherein

R$^1$ is $R^5$—S(=O)$_2$—, or a nitrogen protecting group selected from the group consisting of acetyl (Ac), trifluoroacetyl (TFA), trichloroacetyl (TCA), tert-butyloxycarbonyl (Boc), carbobenzyloxy (Cbz), vinyloxycarbonyl (Voc), allyloxycarbonyl (Alloc), and 9-fluorenylmethyloxycarbonyl (Fmoc);

R$^2$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, wherein one or more hydrogen is optionally substituted by an optionally substituted aryl, heteroaryl, $C_3$-$C_{10}$ cycloalkyl, $C_3$-$C_{10}$ hetero cycloalkyl, F, Cl, Br, I, hydroxyl, $C_1$-$C_8$ alkoxyl, amino group, or NHBoc, or R$^2$ may form a fused ring with one adjacent carbon atom next to the nitrogen that R$^2$ is attached;

R$^3$ and R$^4$ are each independently H, optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, or an electro withdrawing group (EWG), wherein at least one of R$^3$ and R$^4$ is an electro withdrawing group;

R$^5$ is optionally substituted $C_1$-$C_{12}$ straight or branched alkyl, $C_1$-$C_{12}$ alkenyl, $C_1$-$C_{12}$ alkynyl, $C_3$-$C_{10}$ cycloalkyl, $C_3$-$C_{10}$ hetero cycloalkyl, aryl, heteroaryl;

R$^6$ is H, nitro, F, Cl, Br, I, amino, cyano, $C_1$-$C_4$ straight, branched, or cycloalkyl, $C_1$-$C_4$ trifluoroalkyl, hydroxyl, $C_1$-$C_4$ alkoxyl, or —SH;

R$^7$ is H, $C_1$-$C_4$ straight, branched, or cycloalkyl; and

X is a $C_2$-$C_4$ saturated carbon linker, wherein $C_2$-$C_4$ saturated carbon linker is optionally substituted with 4-8 hydrogen, 4-8 optionally substituted $C_1$-$C_{12}$ straight or branched alkyl, wherein one of the 4-8 optionally substituted $C_1$-$C_{12}$ straight or branched alkyl may form a fused ring with the $C_2$-$C_4$ saturated carbon linker or with R$_1$, or from a spiro ring with the carbon atom on the $C_2$-$C_4$ saturated carbon linker that the straight or branched alkyl is attached.

In one embodiment, the present invention provides a method of preparing a compound of Formula II from a compound of Formula I, wherein the reaction comprising the use of an appropriate nucleophile and an appropriate electrophile compound. In one aspect, an appropriate nucleophile may be but is not limited to a compound that may provide a hydride ion. In one aspect, a compound that may provide a hydride ion may be but is not limited to NaBH$_3$CN. In one aspect, an appropriate electrophile compound may be any compound that may provide proton (H$^+$), for example, water or acetic acid.

In one embodiment, the present disclosure provides a method of preparing the compound of Formula II through the preparation of the compound of Formula I, wherein the method may be a two-step one pot reaction, wherein the compound of Formula I is not separated and/or purified when the compound of Formula I is prepared and converted to the compound of Formula II.

EXPERIMENTAL SECTIONS

General Procedure for Syntheses of Starting Material Diamines of R$^1$NHXNYR$^2$ The starting material 1,2-diamines with a general formula of R$^1$NHXNYR$^2$ can be purchased if commercial available or prepared according to literature publications. The general procedures for syntheses of starting material 1,2-diamines can be found in Squires, C., Baxter, C. W., Campbell, J., Lindoy, L. F., McNab, H., Parkin, A., Parsons, S., Tasker, P. A., Wei, G. & White, D. J. Design of base metal extractants. Part 1. Inter-ligand hydrogen bonding in the assembly of pseudo-macrocyclic bis(aminosulfonamidato)M(II) complexes. *Dalton Trans.* 2026-2034 (2006).

A Representative Procedure to Prepare Diamines with Formula of R$^1$NHXNYR$^2$:

A reaction mixture of a terminal unsubstituted diamine (10 mmol), an aldehyde (10 mmol) or ketone (10 mmol) and dry 4 Å molecular sieve (5.0 g) in dry MeOH (20 mL) was stirred for overnight under argon at room temperature. Then the reaction was then cooled to 0° C. before NaBH$_4$ (15 mmol) was added slowly. The reaction process was monitored by TLC. Upon full conversion of the starting material, the 4 Å molecular sieve was removed by filtration. Added dichloromethane (DCM, 100 mL) and water to the filtrate. The organic layer was separated and the aqueous phase was further extracted with DCM three times. The combined organic extracts were dried over Na$_2$SO$_4$, filtered, and concentrated in vacuo. The crude residue was purified on a silica gel column (the silica gel was pre-treated with Et$_3$N) with hexane/EtOAc as the eluents to give the desired products as the starting material diamines with the formula of R$^1$NHXNYR$^2$.

General Procedure for Syntheses of 1.4 Diazo N-heterocycles

Step 1: General Procedure for Syntheses of 1.4 Diazo N-heterocycles of Formula I To a 2-dram vial wrapped with aluminum foil was added a 1 diamine substrate with formula of R$^1$NHXNYR$^2$ (0.1 mmol), NIS (0.105 mmol), and dry THF (1 mL). The reaction mixture was stirred for 1 h under argon before an allene substrate (0.15 mmol) and Cs$_2$CO$_3$ (0.15 mmol) was added and the reaction mixture was let to stir. An intermediate compound of Formula I as previous defined was made at this step.

Examples 1-2 were prepared according to the general procedure for syntheses of 1.4 diazo N-heterocycles of Formula I:

| Preparations | Structures | Chemical names | Physical Data [HRMS (ESI): m/z)] [M + H]$^+$ |
|---|---|---|---|
| 1 | [structure] | Ethyl (E)-2-(1-butyl-4-tosylpiperazin-2-ylidene)acetate | 381.3 |
| 2 | [structure] | Ethyl (E)-2-(1-butyl-4-tosyloctahydroquinoxalin-2(1H)-ylidene)acetate | 435.2 |

The intermediate compound of Formula I may be separated or carried over to the next step without separation/purification.

Step 2: General Procedure for Syntheses of 1.4 Diazo N-Heterocycles of Formula II After the reaction mixture was stirred for 24 h, NaBH$_3$CN (0.2 mmol) and a co-solvent of MeOH/AcOH (pH=4, 1 mL) were added to the reaction mixture with the prepared product of Formula I. After 3 h, the reaction was quenched with a saturated aqueous solution of NaHCO$_3$, extracted with CH$_2$Cl$_2$ for three times. The combined organic extracts were dried over Na$_2$SO$_4$, filtered, and concentrated in vacuo. The crude mixture was purified on silica gel column with hexane/EtOAc as eluents to give the desired 1,4-diazo N-heterocycles with the Formula II such as a piperazine product.

Examples 3-97 were prepared according to the general procedure for syntheses of 1.4 diazo N-heterocycles of Formula II.
| Preparations | Structures | Physical Data [HRMS (ESI): m/z)] [M + H]+ |
|---|---|---|
| 3 | 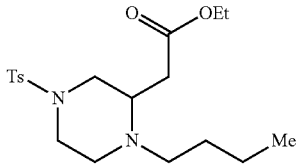 [SMILES: CCCCN1CCN(S(=O)(=O)c2ccc(C)cc2)CC1CC(=O)OCC] | 383.2 |
| 4 | 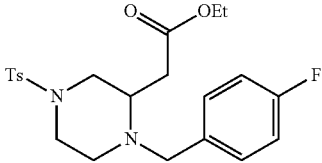 [SMILES: CCOC(=O)CC1CN(S(=O)(=O)c2ccc(C)cc2)CCN1Cc1ccc(F)cc1] | 435.2 |
| 5 | 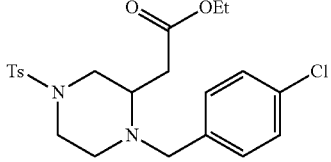 [SMILES: CCOC(=O)CC1CN(S(=O)(=O)c2ccc(C)cc2)CCN1Cc1ccc(Cl)cc1] | 451.1 |
| 6 | 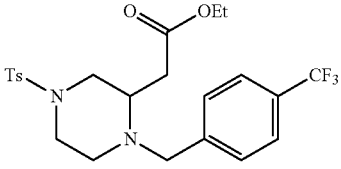 [SMILES: CCOC(=O)CC1CN(S(=O)(=O)c2ccc(C)cc2)CCN1Cc1ccc(C(F)(F)F)cc1] | 485.2 |
| 7 | 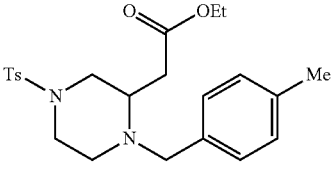 [SMILES: CCOC(=O)CC1CN(S(=O)(=O)c2ccc(C)cc2)CCN1Cc1ccc(C)cc1] | 431.2 |
| 8 | 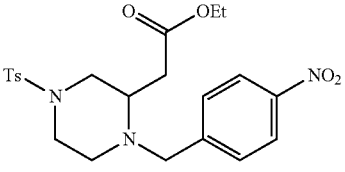 [SMILES: CCOC(=O)CC1CN(S(=O)(=O)c2ccc(C)cc2)CCN1Cc1ccc([N+](=O)[O-])cc1] | 462.2 |
| 9 | 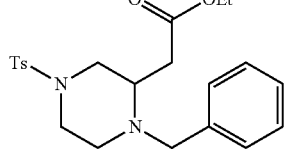 | 417.2 |
| 10 | 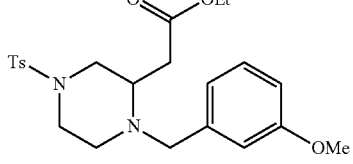 | 447.2 |

-continued

| Preparations | Structures | Physical Data [HRMS (ESI): m/z)] [M + H]+ |
|---|---|---|
| 11 | Ts-piperazine with CH2CO2Et and N-CH2CH2-(3-methoxyphenyl) | 461.2 |
| 12 | Ts-piperazine with CH2CO2Et and N-CH2-(3,5-dimethoxyphenyl) | 477.2 |
| 13 | Ts-piperazine with CH2CO2Et and N-CH2-(2-bromophenyl) | 495.1 |
| 14 | Ts-piperazine with CH2CO2Et and N-CH2-(3-bromophenyl) | 495.1 |
| 15 | Ts-piperazine with CH2CO2Et and N-CH2-(2-pyridyl) | 418.2 |
| 16 | Ts-piperazine with CH2CO2Et and N-CH2-(4-isoquinolinyl) | 468.2 |
| 17 | Ts-piperazine with CH2CO2Et and N-CH2-(2-furyl) | 407.2 |

| Preparations | Structures | Physical Data [HRMS (ESI): m/z)] [M + H]+ |
|---|---|---|
| 18* | (structure) | 506.2 |
| 19* | (structure) | 556.2 |
| 20* | (structure) | 556.2 |
| 21 | (structure) | 423.2 |
| 22 | (structure) | 383.2 |
| 23 | (structure) | 425.2 |
| 24 | (structure) | 371.2 |
| 25 | (structure) | 470.2 |

-continued

| Preparations | Structures | Physical Data [HRMS (ESI): m/z)] [M + H]+ |
|---|---|---|
| 26 | 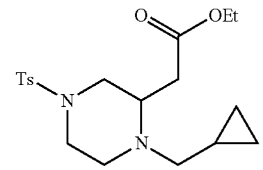 [SMILES: CCOC(=O)CC1CN(S(=O)(=O)c2ccc(C)cc2)CCN1CC1CC1] | 381.2 |
| 27 | 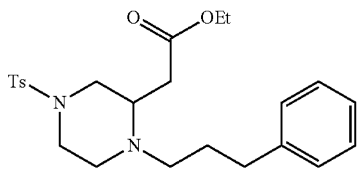 [SMILES: CCOC(=O)CC1CN(S(=O)(=O)c2ccc(C)cc2)CCN1CCCc1ccccc1] | 445.2 |
| 28 | 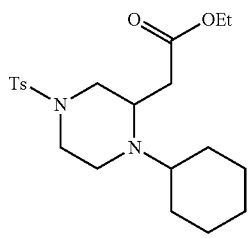 [SMILES: CCOC(=O)CC1CN(S(=O)(=O)c2ccc(C)cc2)CCN1C1CCCCC1] | 409.2 |
| 29 | 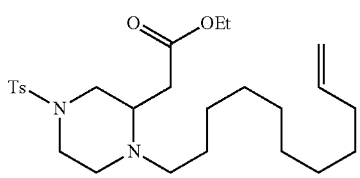 [SMILES: C=CCCCCCCCCCN1CCN(S(=O)(=O)c2ccc(C)cc2)CC1CC(=O)OCC] | 479.3 |
| 30 | 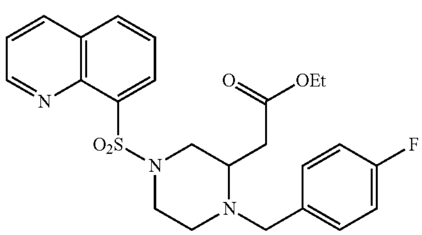 [SMILES: CCOC(=O)CC1CN(S(=O)(=O)c2cccc3cccnc23)CCN1Cc1ccc(F)cc1] | 472.2 |
| 31 | 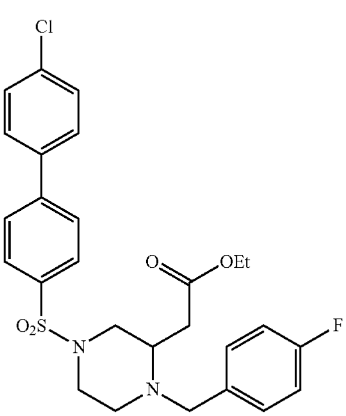 [SMILES: CCOC(=O)CC1CN(S(=O)(=O)c2ccc(-c3ccc(Cl)cc3)cc2)CCN1Cc1ccc(F)cc1] | 531.2 |

-continued

| Preparations | Structures | Physical Data [HRMS (ESI): m/z)] [M + H]+ |
|---|---|---|
| 32 | 4-nitrophenylsulfonyl piperazine with ethyl acetate and N-butyl | 414.2 |
| 33 | 2,3-dihydrobenzo[1,4]dioxine-6-sulfonyl piperazine with ethyl acetate and 4-fluorobenzyl | 479.2 |
| 34 | thiophene-2-sulfonyl piperazine with ethyl acetate and 4-fluorobenzyl | 427.1 |
| 35 | phenylsulfonyl piperazine with ethyl acetate and N-butyl | 369.2 |
| 36 | Ts-piperazine with methyl acetate and N-butyl | 369.2 |
| 37 | Ts-piperazine with benzyl acetate and N-butyl | 445.2 |
| 38 | Ts-piperazine with tert-butyl acetate and N-butyl | 411.2 |

-continued

| Preparations | Structures | Physical Data [HRMS (ESI): m/z)] [M + H]+ |
|---|---|---|
| 39 | *piperazine with Ts on one N, n-butyl on other N, CH2-C(=O)-O-(3-methoxyphenyl) substituent* | 461.2 |
| 40 | *piperazine with Ts, n-butyl, CH2-C(=O)-O-CH2-(3-methoxyphenyl)* | 475.2 |
| 41 | *piperazine with Ts, n-butyl, CH2-C(=O)-Ph* | 415.2 |
| 42 | *piperazine with Ts, n-butyl, CH2-C(=O)-(4-chlorophenyl)* | 449.2 |
| 43 | *piperazine with Ts, n-butyl, CH2-C(=O)-(4-fluorophenyl)* | 433.2 |
| 44 | *piperazine with Ts, n-butyl, CH2-C(=O)-(4-methoxyphenyl)* | 445.2 |
| 45 | *piperazine with Ts, n-butyl, CH2-C(=O)-(4-trifluoromethylphenyl)* | 483.2 |

-continued
| Preparations | Structures | Physical Data [HRMS (ESI): m/z)] [M + H]+ |
|---|---|---|
| 46 | 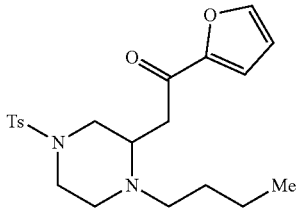 [SMILES: CCCCN1CCN(S(=O)(=O)c2ccc(C)cc2)CC1CC(=O)c1ccco1] | 405.2 |
| 47 | 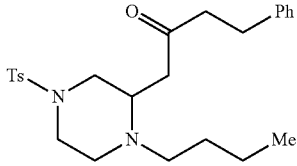 | 443.2 |
| 48 | 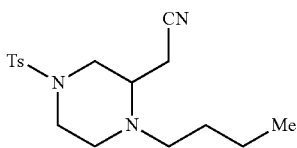 [SMILES: CCCCN1CCN(S(=O)(=O)c2ccc(C)cc2)CC1CC#N] | 336.2 |
| 49 | 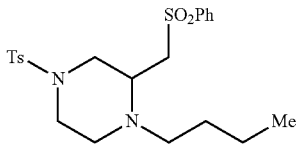 | 451.2 |
| 50 | 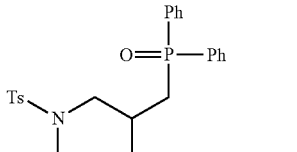 | 511.2 |
| 51 | 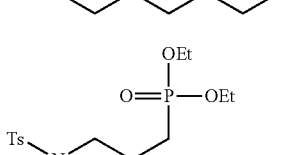 | 447.2 |
| 52 | 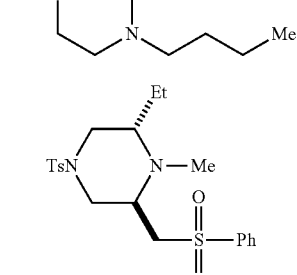 | 437.2 |
| 53 | 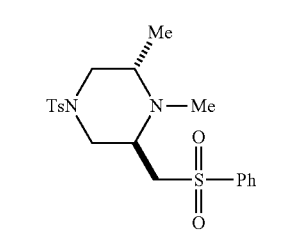 [SMILES: Cc1ccc(S(=O)(=O)N2C[C@H](CS(=O)(=O)c3ccccc3)N(C)[C@@H](C)C2)cc1] | 423.1 |

| Preparations | Structures | Physical Data [HRMS (ESI): m/z)] [M + H]+ |
|---|---|---|
| 54 | (structure) | |
| 55 | (structure) | 461.2 |
| 56 | (structure) | 465.2 |
| 57 | (structure) | 527.2 |
| 58 | (structure) | 485.2 |
| 59 | (structure) | 417.2 |
| 60 | (structure) | 505.2 |

-continued

| Preparations | Structures | Physical Data [HRMS (ESI): m/z)] [M + H]+ |
|---|---|---|
| 61 | 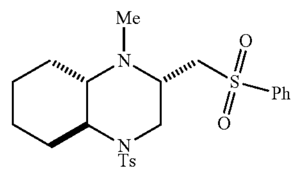 | 463.6 |
| 62 | 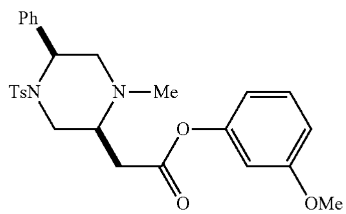 [SMILES: COc1cccc(OC(=O)C[C@H]2CN(S(=O)(=O)c3ccc(C)cc3)[C@@H](c3ccccc3)CN2C)c1] | 495.2 |
| 63 | 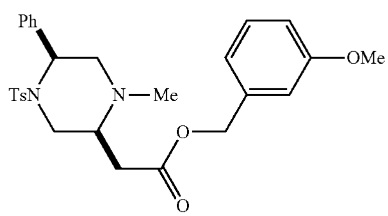 [SMILES: COc1cccc(COC(=O)C[C@H]2CN(S(=O)(=O)c3ccc(C)cc3)[C@@H](c3ccccc3)CN2C)c1] | 509.2 |
| 64 | 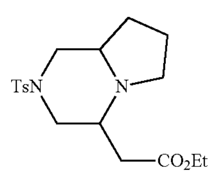 [SMILES: CCOC(=O)CC1CN(S(=O)(=O)c2ccc(C)cc2)CC2CCCN21] | 367.2 |
| 65 | 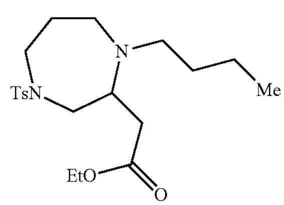 [SMILES: CCCCN1CCCN(S(=O)(=O)c2ccc(C)cc2)CC1CC(=O)OCC] | 397.2 |
| 66 | 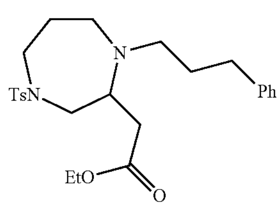 [SMILES: CCOC(=O)CC1CN(S(=O)(=O)c2ccc(C)cc2)CCCN1CCCc1ccccc1] | 459.2 |
| 67 | 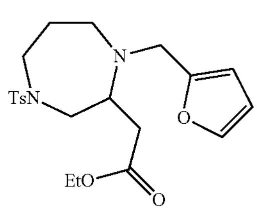 [SMILES: CCOC(=O)CC1CN(S(=O)(=O)c2ccc(C)cc2)CCCN1Cc1ccco1] | 421.2 |

-continued

| Preparations | Structures | Physical Data [HRMS (ESI): m/z)] [M + H]+ |
|---|---|---|
| 68 | 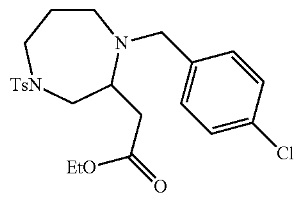 [SMILES: CCOC(=O)CC1CN(S(=O)(=O)c2ccc(C)cc2)CCCN1Cc1ccc(Cl)cc1] | 465.2 |
| 69 | 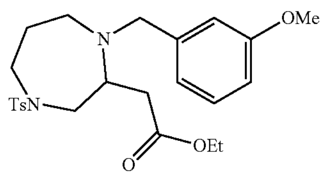 [SMILES: CCOC(=O)CC1CN(S(=O)(=O)c2ccc(C)cc2)CCCN1Cc1cccc(OC)c1] | 461.2 |
| 70 | 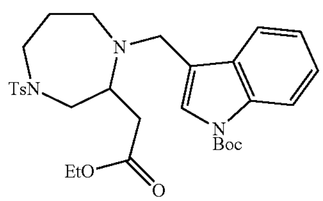 [SMILES: CCOC(=O)CC1CN(S(=O)(=O)c2ccc(C)cc2)CCCN1Cc1cn(C(=O)OC(C)(C)C)c2ccccc12] | 570.3 |
| 71 | 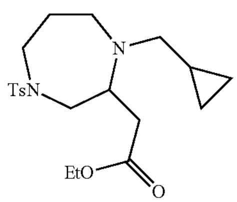 [SMILES: CCOC(=O)CC1CN(S(=O)(=O)c2ccc(C)cc2)CCCN1CC1CC1] | 395.2 |
| 72 | 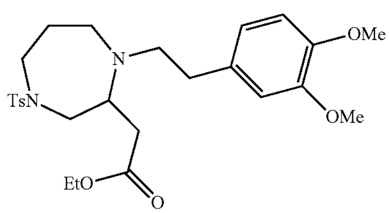 [SMILES: CCOC(=O)CC1CN(S(=O)(=O)c2ccc(C)cc2)CCCN1CCc1ccc(OC)c(OC)c1] | 505.2 |
| 73 | 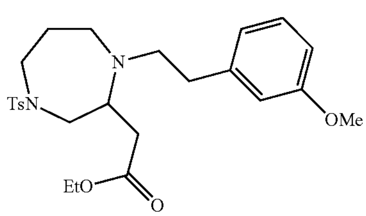 [SMILES: CCOC(=O)CC1CN(S(=O)(=O)c2ccc(C)cc2)CCCN1CCc1cccc(OC)c1] | 475.2 |
| 74 | 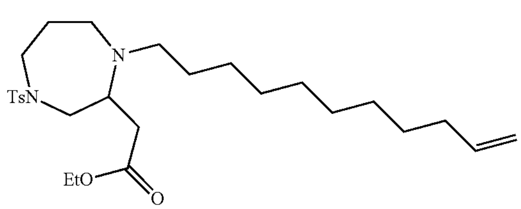 [SMILES: C=CCCCCCCCCCN1CCCN(S(=O)(=O)c2ccc(C)cc2)CC1CC(=O)OCC] | 493.3 |

| Preparations | Structures | Physical Data [HRMS (ESI): m/z)] [M + H]+ |
|---|---|---|
| 75 | 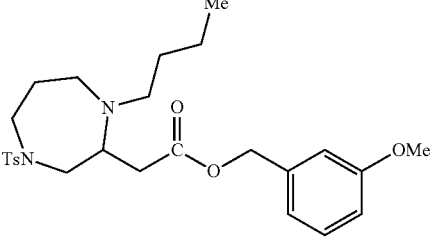 | 489.2 |
| 76 | 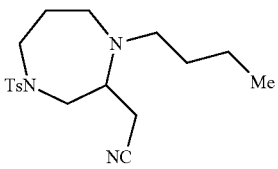 [SMILES: CCCCN1CCCN(S(=O)(=O)c2ccc(C)cc2)CC1CC#N] | 350.2 |
| 77 | 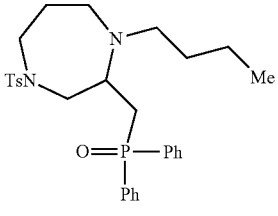 [SMILES: CCCCN1CCCN(S(=O)(=O)c2ccc(C)cc2)CC1CP(=O)(c1ccccc1)c1ccccc1] | 525.2 |
| 78 | 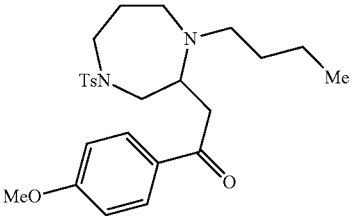 [SMILES: CCCCN1CCCN(S(=O)(=O)c2ccc(C)cc2)CC1CC(=O)c1ccc(OC)cc1] | 459.2 |
| 79 | 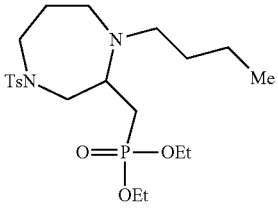 [SMILES: CCCCN1CCCN(S(=O)(=O)c2ccc(C)cc2)CC1CP(=O)(OCC)OCC] | 461.2 |
| 80 | 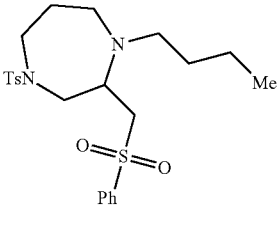 [SMILES: CCCCN1CCCN(S(=O)(=O)c2ccc(C)cc2)CC1CS(=O)(=O)c1ccccc1] | 465.2 |
| 81 | 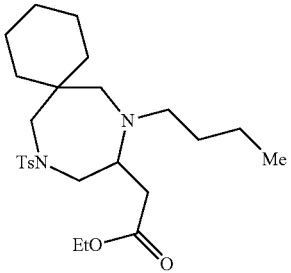 [SMILES: CCCCN1CC2(CCCCC2)CN(S(=O)(=O)c2ccc(C)cc2)CC1CC(=O)OCC] | 465.3 |

-continued
| Preparations | Structures | Physical Data [HRMS (ESI): m/z)] [M + H]+ |
|---|---|---|
| 82 | 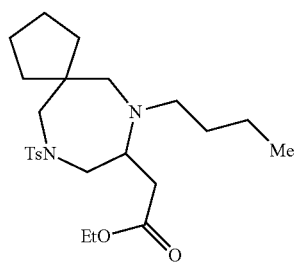 [SMILES: CCCCN1CC2(CCCC2)CN(S(=O)(=O)c2ccc(C)cc2)CC1CC(=O)OCC] | 451.3 |
| 83 | 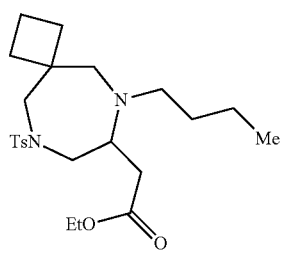 [SMILES: CCCCN1CC2(CCC2)CN(S(=O)(=O)c2ccc(C)cc2)CC1CC(=O)OCC] | 437.2 |
| 84 | 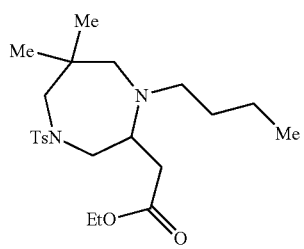 [SMILES: CCCCN1CC(C)(C)CN(S(=O)(=O)c2ccc(C)cc2)CC1CC(=O)OCC] | 425.2 |
| 85 | 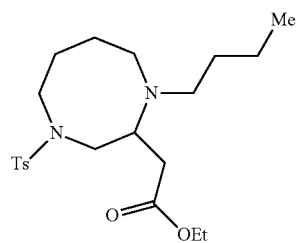 [SMILES: CCCCN1CCCCN(S(=O)(=O)c2ccc(C)cc2)CC1CC(=O)OCC] | 411.2 |
| 86 | 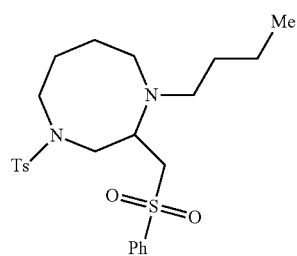 [SMILES: CCCCN1CCCCN(S(=O)(=O)c2ccc(C)cc2)CC1CS(=O)(=O)c1ccccc1] | 479.2 |

-continued
| Preparations | Structures | Physical Data [HRMS (ESI): m/z)] [M + H]+ |
|---|---|---|
| 87 | 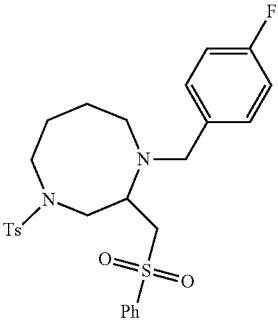 [SMILES: Cc1ccc(S(=O)(=O)N2CCCCN(Cc3ccc(F)cc3)C(CS(=O)(=O)c3ccccc3)C2)cc1] | 531.2 |
| 88 | 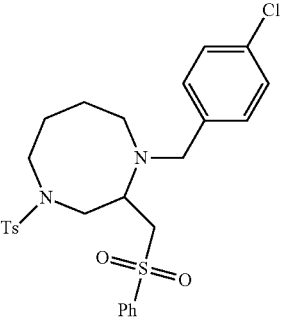 [SMILES: Cc1ccc(S(=O)(=O)N2CCCCN(Cc3ccc(Cl)cc3)C(CS(=O)(=O)c3ccccc3)C2)cc1] | 547.1 |
| 89 | 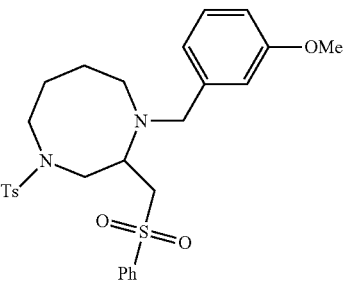 [SMILES: COc1cccc(CN2CCCCN(S(=O)(=O)c3ccc(C)cc3)CC2CS(=O)(=O)c2ccccc2)c1] | 543.2 |
| 90 | 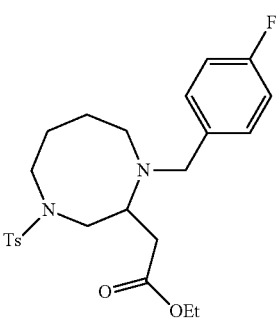 [SMILES: CCOC(=O)CC1CN(S(=O)(=O)c2ccc(C)cc2)CCCCN1Cc1ccc(F)cc1] | 463.2 |
| 91 | 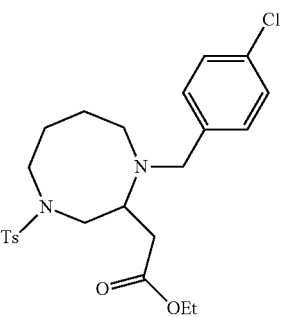 [SMILES: CCOC(=O)CC1CN(S(=O)(=O)c2ccc(C)cc2)CCCCN1Cc1ccc(Cl)cc1] | 479.2 |

-continued
| Preparations | Structures | Physical Data [HRMS (ESI): m/z)] [M + H]+ |
|---|---|---|
| 92 | 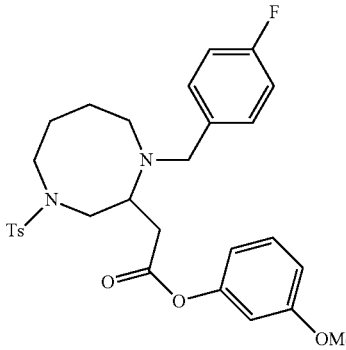 | 541.2 |
| 93 | 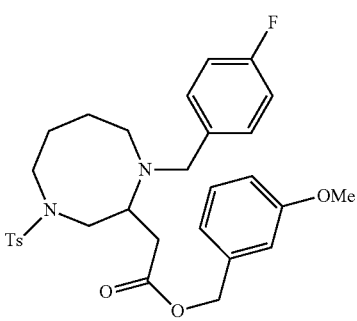 [SMILES: COc1cccc(COC(=O)CC2CN(S(=O)(=O)c3ccc(C)cc3)CCCCN2Cc2ccc(F)cc2)c1] | 555.2 |
| 94 | 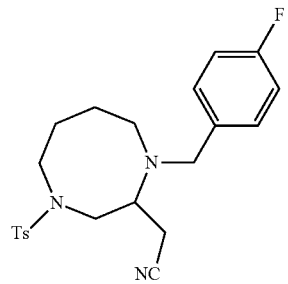 [SMILES: Cc1ccc(S(=O)(=O)N2CCCCN(Cc3ccc(F)cc3)C(CC#N)C2)cc1] | 416.2 |
| 95 | 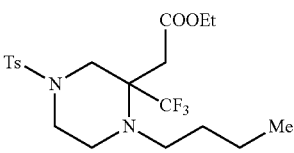 [SMILES: CCCCN1CCN(S(=O)(=O)c2ccc(C)cc2)CC1(CC(=O)OCC)C(F)(F)F] | 451.2 |
| 96 | 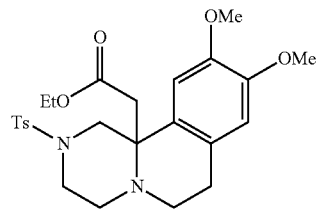 [SMILES: CCOC(=O)CC12CN(S(=O)(=O)c3ccc(C)cc3)CCN1CCc1cc(OC)c(OC)cc12] | 489.2 |
| 97 | 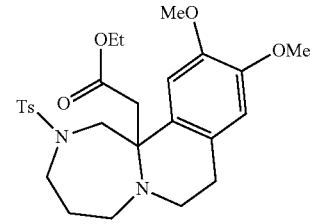 [SMILES: CCOC(=O)CC12CN(S(=O)(=O)c3ccc(C)cc3)CCCN1CCc1cc(OC)c(OC)cc12] | 503.2 |

Those skilled in the art will recognize that numerous modifications can be made to the specific implementations described above. The implementations should not be limited to the particular limitations described. Other implementations may be possible.

We claim:

1. A compound of formula II:

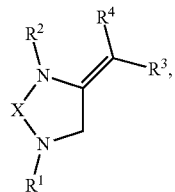

or any salt thereof, wherein

R$^1$ is R$^5$—S(=O)$_2$—;

R$^2$ is optionally substituted C$_1$-C$_{12}$ straight or branched alkyl, C$_1$-C$_{12}$ alkenyl, C$_1$-C$_{12}$ alkynyl, C$_3$-C$_{10}$ cycloalkyl, C$_3$-C$_{10}$ hetero cycloalkyl, wherein one or more hydrogen of said C$_1$-C$_{12}$ straight or branched alkyl, C$_1$-C$_{12}$ alkenyl, C$_1$-C$_{12}$ alkynyl, C$_3$-C$_{10}$ cycloalkyl, or C$_3$-C$_{10}$ hetero cycloalkyl is optionally replaced by an optionally substituted aryl, heteroaryl, C$_3$-C$_{10}$ cycloalkyl, C$_3$-C$_{10}$ hetero cycloalkyl, F, Cl, Br, I, hydroxyl, C$_1$-C$_8$ alkoxyl, amino group, or NHBoc, or R$^2$ can form a fused ring with one adjacent carbon atom next to the nitrogen that R$^2$ is attached;

R$^3$ and R$^4$ are each independently H, optionally substituted C$_1$-C$_{12}$ straight or branched alkyl, C$_1$-C$_{12}$ alkenyl, C$_1$-C$_{12}$ alkynyl, C$_3$-C$_{10}$ cycloalkyl, C$_3$-C$_{10}$ hetero cycloalkyl, or an electro withdrawing group (EWG), wherein at least one of R$^3$ and R$^4$ is an electro withdrawing group, wherein the electro withdrawing group (EWG) is selected from the group consisting of methoxycarbonyl, ethoxycarbonyl, butoxycarbonyl, t-butoxycarbonyl, phenoxycarbonyl, (3-methoxyphenoxy)carbonyl, ((3-methoxybenzyl)oxy)carbonyl, furan-2-carbonyl, benzoyl, fluorobenzoyl, chlorobenzoyl, methoxybenzoyl, trifluoromethylbenzoyl, diethoxyphosphoryl, diphenylphosphoryl, phenylsulfonyl, cyano, and 2-oxy-4-phenylbutyl;

R$^5$ is selected from the group consisting of:

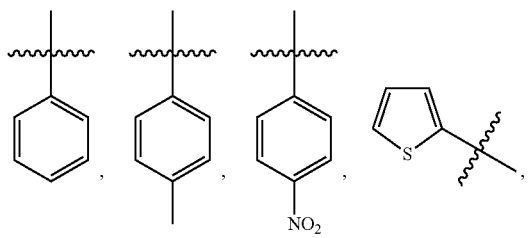

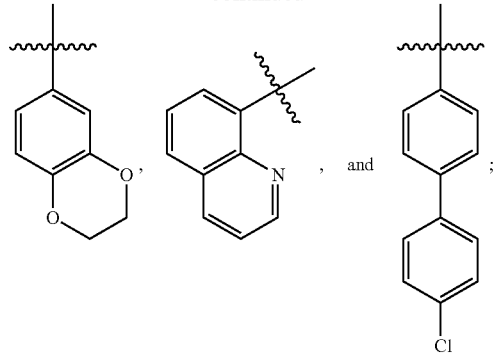

R$^6$ is H, nitro, F, Cl, Br, I, amino, cyano, C$_1$-C$_4$ straight, branched, or cycloalkyl, C$_1$-C$_4$ trifluoroalkyl, hydroxyl, C$_1$-C$_4$ alkoxyl, or —SH;

R$^7$ is H, C$_1$-C$_4$ straight, branched, or cycloalkyl; and

X is a C$_2$-C$_4$ saturated carbon linker, wherein C$_2$-C$_4$ saturated carbon linker is optionally substituted with C$_1$-C$_{12}$ straight or branched alkyl, wherein one of the 4-8 C$_1$-C$_{12}$ straight or branched alkyl can form a fused ring with the C$_2$-C$_4$ saturated carbon linker or with R$_1$, or from a spiro ring with the carbon atom on the C$_2$-C$_4$ saturated carbon linker that the straight or branched alkyl is attached.

2. The compound of claim 1, wherein R$^2$ is optionally substituted C$_1$-C$_{12}$ straight or branched alkyl, C$_1$-C$_{12}$ alkenyl, C$_3$-C$_{10}$ cycloalkyl, wherein one or more hydrogen of the C$_1$-C$_{12}$ straight or branched alkyl, C$_1$-C$_{12}$ alkenyl, or C$_3$-C$_{10}$ cycloalkyl is optionally replaced with a benzene ring, quinolin ring, pyrrol ring, furan ring, or indole ring, wherein the benzene ring, quinolin ring, pyrrol ring, furan ring, or indole ring is further optionally substituted with 1-3 C$_1$-C$_6$ alkyl, halide, C$_1$-C$_4$ alkoxyl, trihalide methyl, or nitro group.

3. The compound of claim 1, wherein the compound is selected from the group consisting of:

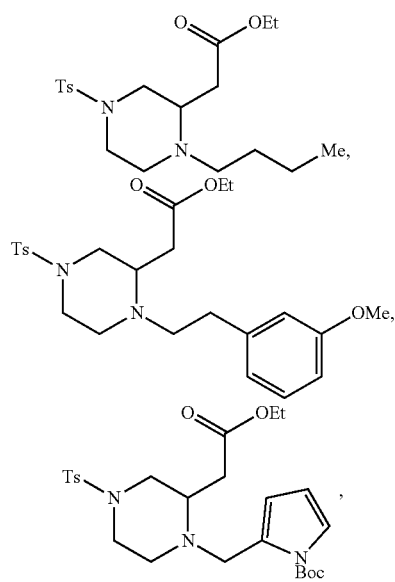

-continued
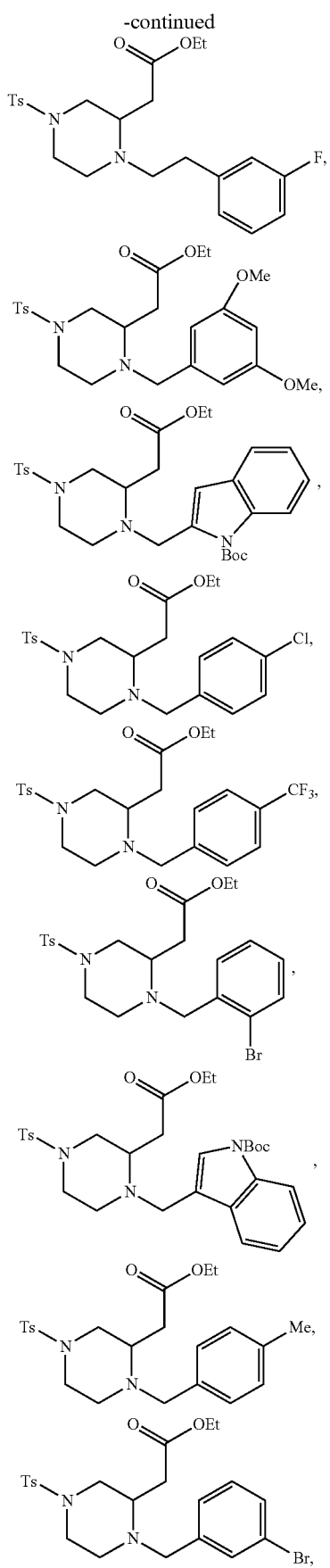
-continued
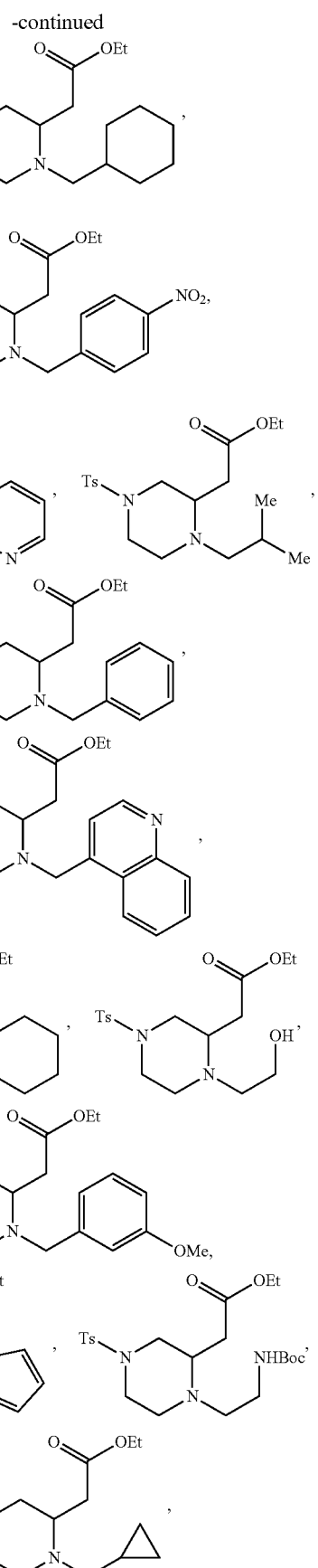

55
-continued
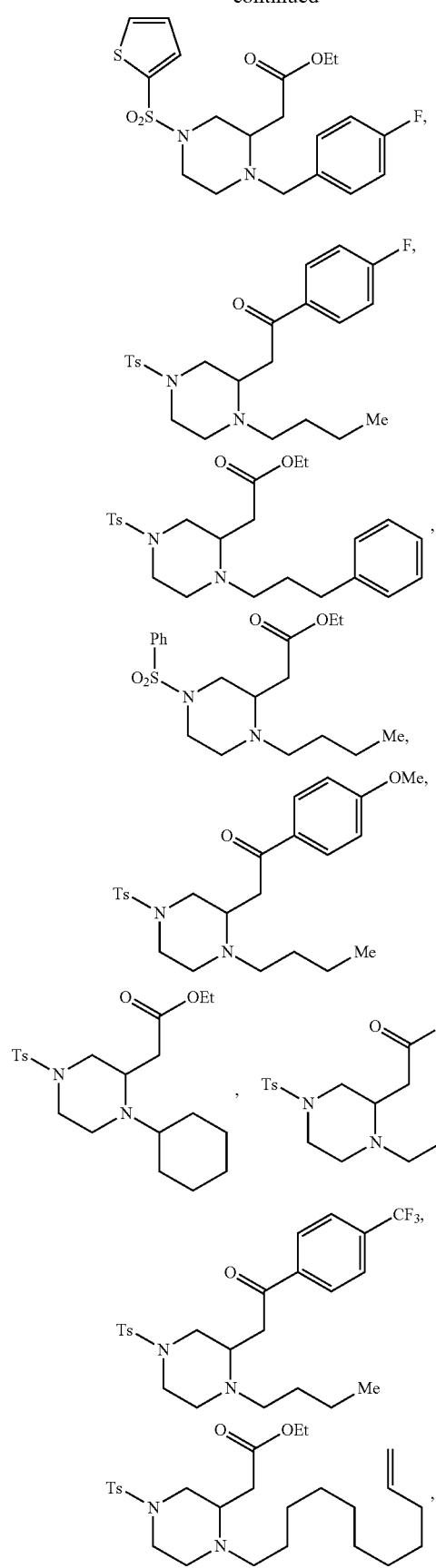
56
-continued
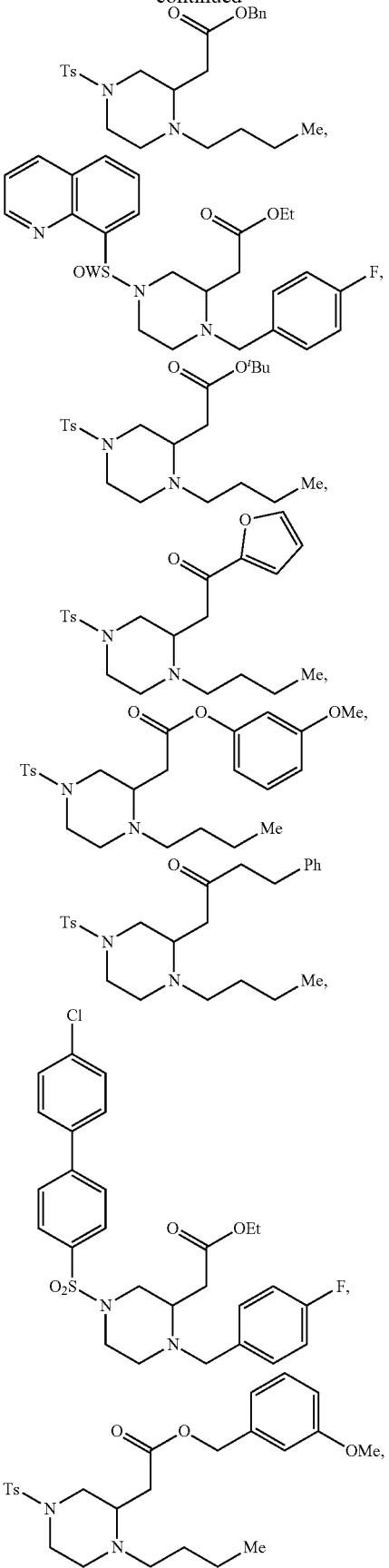

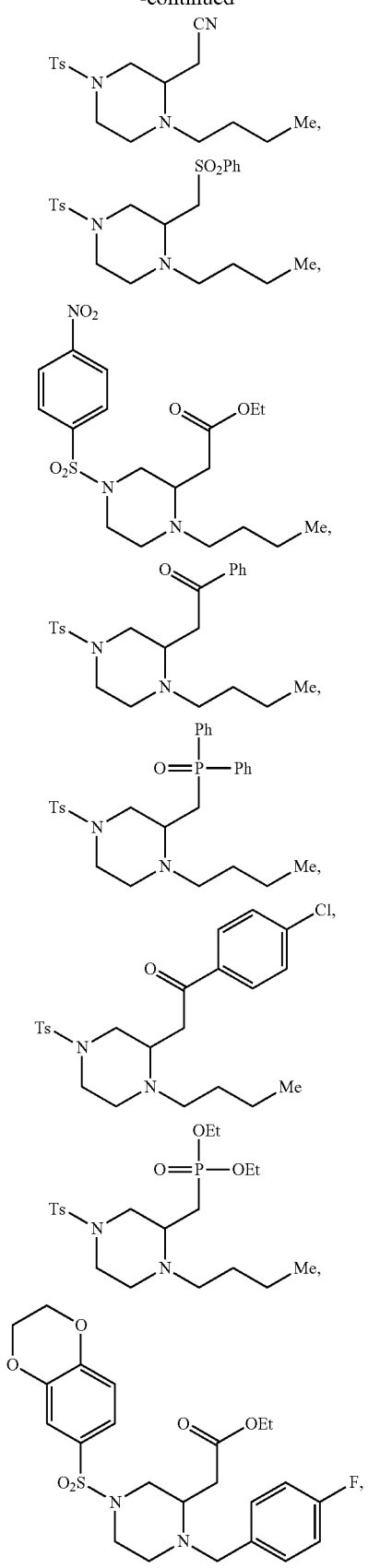
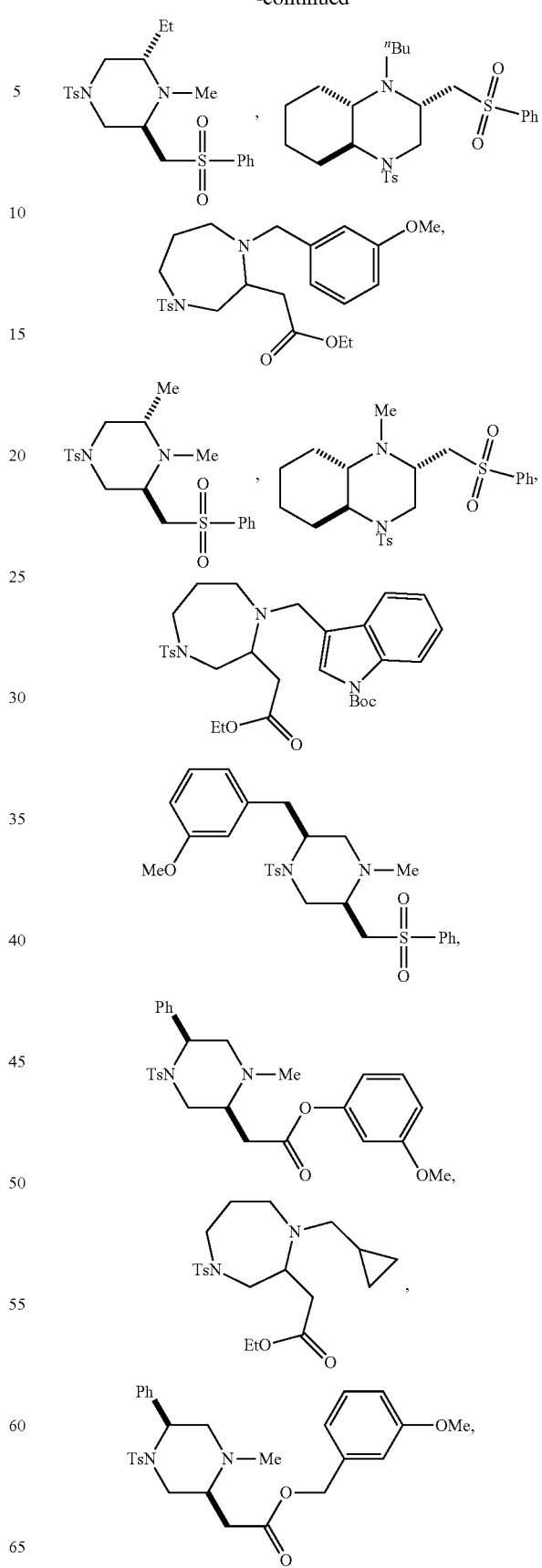

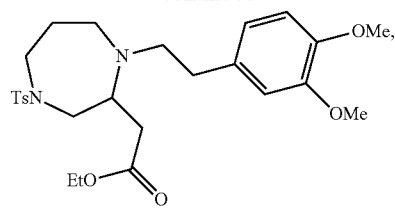
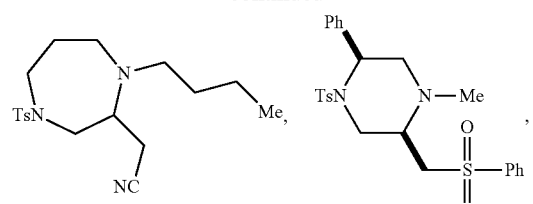
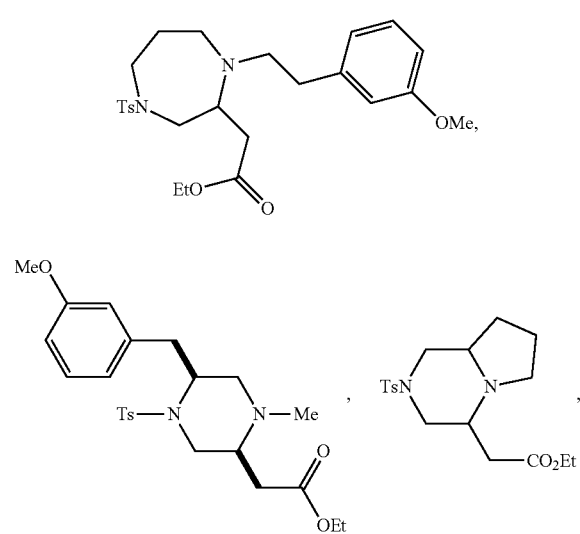
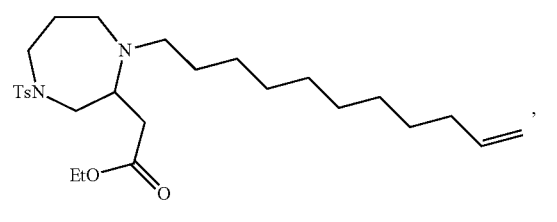
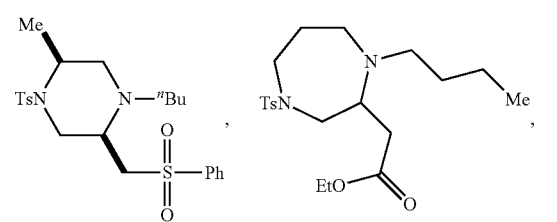
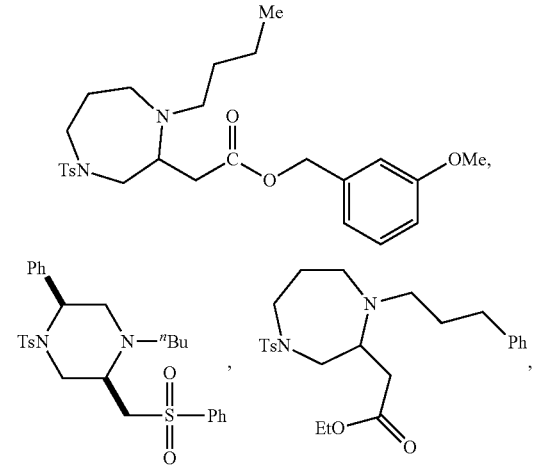

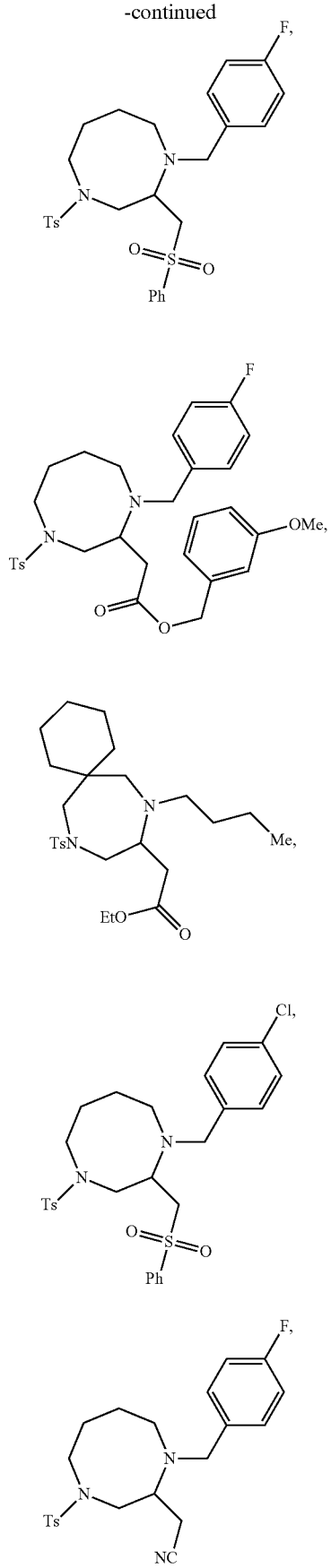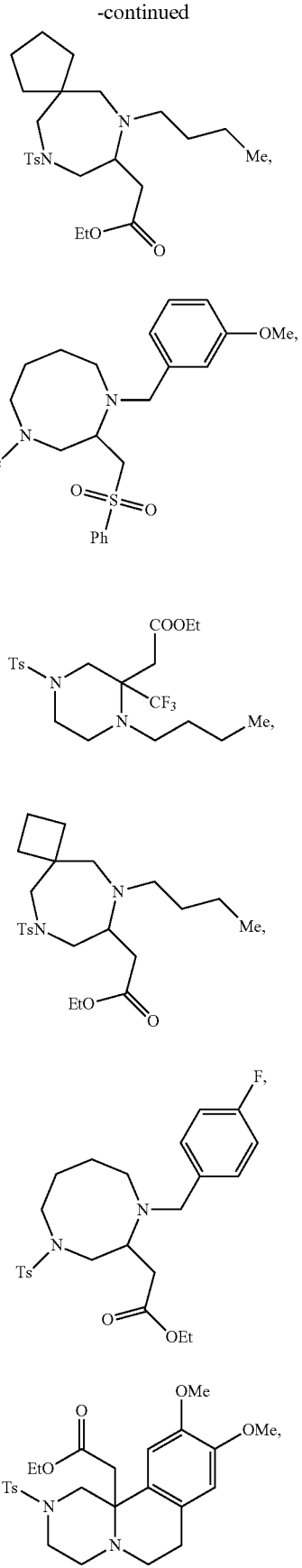

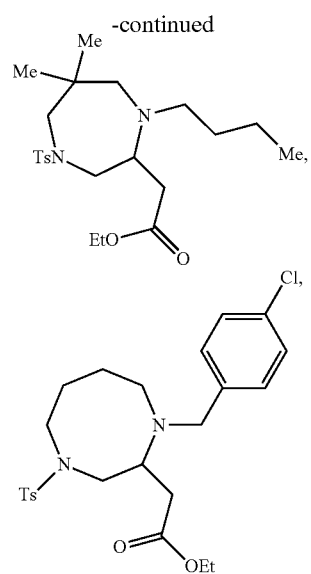
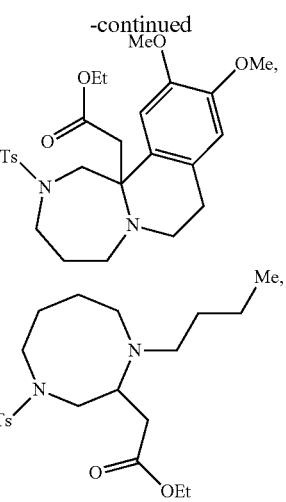
any salt thereof.
* * * * *